United States Patent [19]

Plat et al.

[11] 3,987,049

[45] Oct. 19, 1976

[54] ESTERS OF DIHYDROAPOVINCAMINIC ACID

[75] Inventors: Michel Marie Rene Plat; Monique Plat nee Berry, both of Antony, France

[73] Assignee: Synthelabo, Paris, France

[22] Filed: Jan. 31, 1975

[21] Appl. No.: 545,909

[30] Foreign Application Priority Data

Jan. 31, 1974  France .............................. 74.03167

[52] U.S. Cl. ............................. 260/293.53; 424/267
[51] Int. Cl.² ...................................... C07D 401/14
[58] Field of Search ................. 260/293.53; 424/267

[56] References Cited
UNITED STATES PATENTS

| | | | |
|---|---|---|---|
| 3,770,724 | 11/1973 | Warnant et al. ............... | 260/293.53 |
| 3,884,927 | 5/1975 | Martel et al. .................. | 260/293.53 |

FOREIGN PATENTS OR APPLICATIONS

| | | | |
|---|---|---|---|
| 2,253,750 | 5/1973 | Germany ...................... | 260/293.53 |
| 2,326,301 | 12/1973 | Germany ...................... | 260/293.53 |

OTHER PUBLICATIONS

Bláha et al. Collection Czechoslov. Chem. Commun. 1968, vol. 33, pp. 3833-3847.
Omnium Chimique Chem. Abst. 1973, vol. 78, No. 30049a.

Primary Examiner—Natalie Trousof
Attorney, Agent, or Firm—Armstrong, Nikaido & Wegner

[57] ABSTRACT

The invention relates to esters of general formula (I)

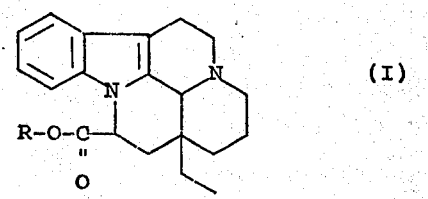

in which R represents a straight or branched saturated or unsaturated aliphatic hydrocarbon group containing 2 to 6 carbon atoms optionally bearing 1 or 2 substituents which substituents may be the same or different and each represents a hydroxyl group or an alkoxy group whose alkyl portion is linear or branched and contains 1 to 6 carbon atoms, and their pharmaceutically acceptable acid addition salts, to processes for their preparation and to pharmaceutical compositions containing them. The esters and salts are suitable for the treatment of vascular and cerebral disorders.

3 Claims, No Drawings

ESTERS OF DIHYDROAPOVINCAMINIC ACID

The present invention relates to certain esters of 16,17-dihydroapovincaminic acid (also known as desoxyvincaminic acid) in their various stereoisomeric forms, their addition salts with pharmaceutically tolerated inorganic and organic acids, their preparation and pharmaceutical compositions containing them.

More specifically, the present invention provides a compound of general formula (I)

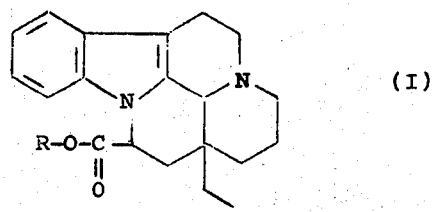

in which R represents a straight or branched, saturated or unsaturated aliphatic hydrocarbon group containing 2 to 6 carbon atoms, optionally bearing 1 or 2 substituents which substituents may be the same or different and each represents a hydroxyl group or an alkoxy group whose alkyl portion is linear or branched and contains 1 to 6 carbon atoms, or a pharmaceutically acceptable acid addition salt thereof.

The compounds of the invention can be used in human and veterinary therapy, especially in the treatment of vascular affections and more especially cerebral disorders.

They can be prepared by known processes; in particular by processes involving the reactions illustrated by the following reaction scheme:

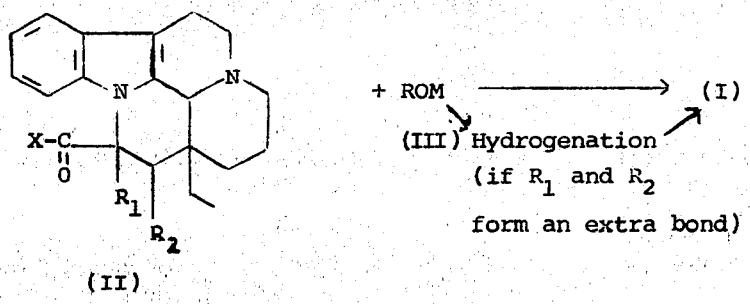

In the formula (II), X represents a hydroxyl radical or a halogen atom and $R_1$ and $R_2$ either each represents a hydrogen atom (in which case (II) is dihydroapovincaminic acid or one of its halides), or, considered together, form an additional bond (in which case, (II) is apovincaminic acid or one of its halides).

In the formula (III), R has the same meaning as in the formula (I) and M represents a hydrogen atom or an alkali metal atom.

When $R_1$ and $R_2$ each represents a hydrogen atom, the compound of formula (I) is obtained directly; if they together represent an additional bond, the process involves the subsequent step of reducing the double bond in order to obtain the compound of formula (I).

The acid halides of formula (II) (in which X = halogen) can be prepared by conventional methods, for example, by converting the acid or its methyl ester to its halide by means of an oxalyl halide, a thionyl halide (for example thionyl chloride) or a halogenated derivative of phosphorus. This acid halide, which may or may not be isolated from the reaction mixture, may then be converted to the ester of formula (I) by reaction with a suitable alkali metal alcoholate or alcohol.

Esterification of an acid of formula (II) (in which X = OH) is preferably carried out using an alcohol of formula (III) (in which M = H). It is advantageously carried out in an acid medium.

When the two-stage process is used, i.e. apovincaminic acid or one of its functional derivatives is first esterified and then the double bond is hydrogenated, the reduction is carried out by a standard chemical or catalytic process, for example with hydrogen in the presence of palladium chloride.

Other types of process which may be used for the preparation of compounds of formula (I) are the following:

a. A process comprising converting the acid of formula (IIa)

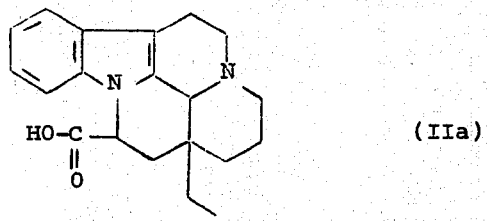

or its methyl ester into an alkali metal salt in known manner and reacting the salt with a halide of formula R—X' in which X' is a halogen atom and R is as defined above, b. A process comprising reacting an acid halide of general formula (IIb)

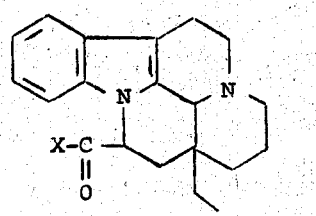

in which X represents a halogen atom, with a cyclic ether of general formula (IV)

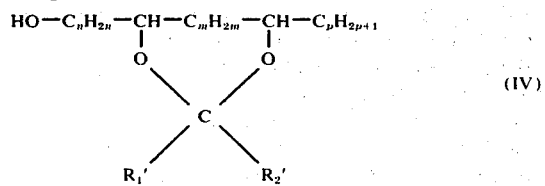

in which n, m and p each independently represents zero or an integer of at most 4, subject to the proviso that $n + m + p$ is at most 4, and $R_1'$ and $R_2'$, which may be the same or different, each represents a lower alkyl group, and hydrolysing the resulting cyclic ester. In this case the product has the formula (Ia)

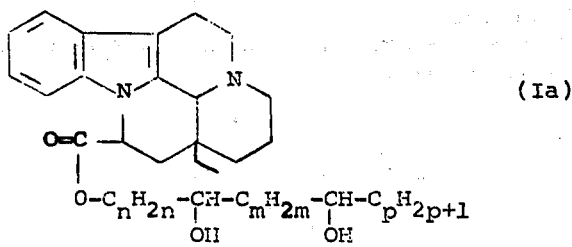

in which m, n and p are as defined above.

Some of the processes referred to above are illustrated in the following reaction scheme in which R is as defined above, M represents an alkali metal atom, especially sodium or potassium, X' represents a halogen atom, especially chlorine or bromine, Y represents a hydrogen atom or a methyl radical, $R_1'$ and $R_2'$, each independently represents a lower alkyl radical and are preferably both methyl radicals, and n, m and p are as defined above.

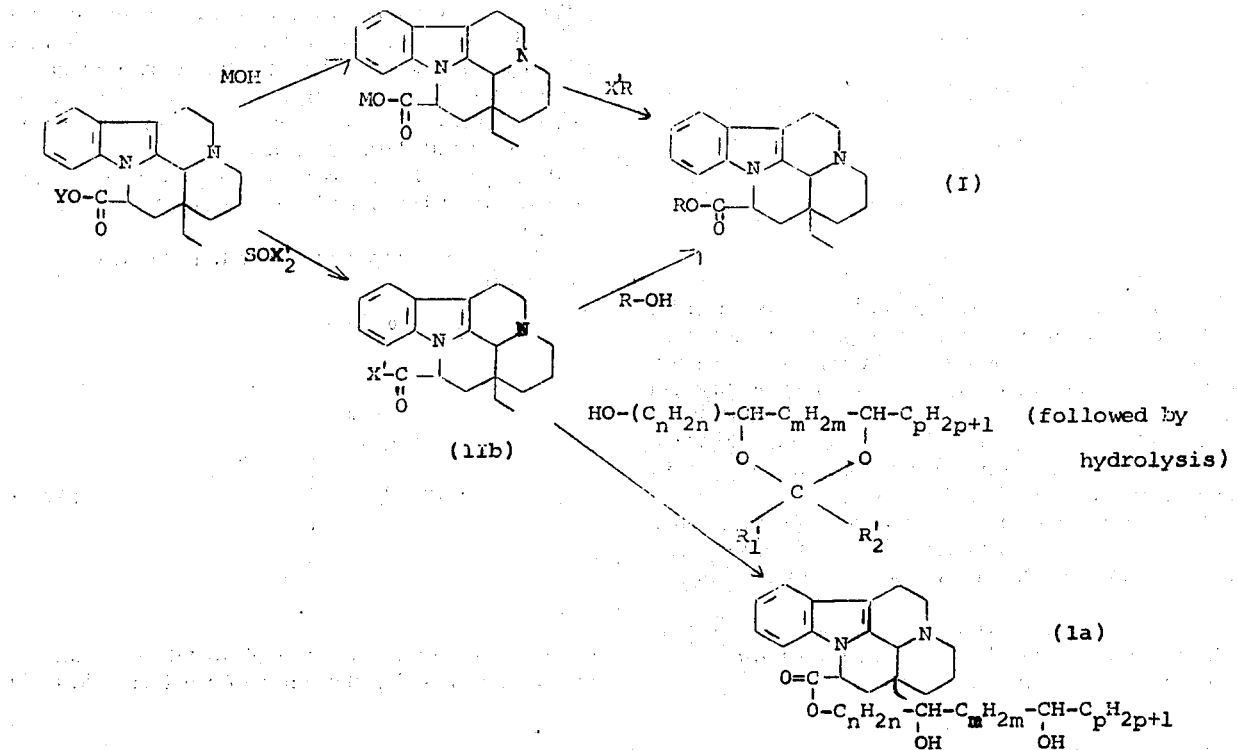

The invention is illustrated by the following Examples.

EXAMPLE 1

2'-Hydroxypropyl 16,17-dihydroapovincaminate and its hemi-malate

[R = —CH$_2$—CH—CH$_3$ ; code number : SL B-826]
              |
              OH A single portion of 4.20 ml (0.05 mol) of oxalyl chloride is added, at a low temperature and with mechanical stirring, to a suspension of 12.976 g (0.04 mol) of 16,17-dihydroapovincaminic acid in 150 ml of anhydrous benzene free from thiophene. The mixture is left to stand overnight. The excess oxalyl chloride and the solvent are removed by distillation under reduced pressure, at 30° – 35° C., in a nitrogen atmosphere, until a residue forming approximately one quarter of the original volume is obtained. The crude 16,17-dihydroapovincaminic acid chloride thus obtained is treated with 3.99 g of 1,2-dihydroxy-propane whose hydroxyl group in the 1-position is in the form of its sodium derivative. The mixture is kept at 20°–25° C for a few hours, and then the reaction is allowed to proceed to completion over the course of 18 hours at at least ambient temperature. The reaction mixture is then cooled to 10° C and is rendered alkaline (pH=10) by means of a dilute solution of ammonia. The benzene phase is isolated by decanting, and the aqueous phase is extracted several times using chloroform or methylene chloride. These extracts are then combined with the benzene phase and the mixture is dried over anhydrous sodium sulphate. After filtration, the solvents are removed on a warm water bath, under reduced pressure.

13.30 g of a dark yellow residue, which is crude 2'-hydroxypropyl 16,17-dihydroapovincaminate, are collected (yield = 87%).

This residue is purified by chromatography on a column of alumina II or III (3 to 6% of water), eluting with ethyl ether. A fraction, weighing 7.02 g (yield = 52%), of pure 2'-hydroxypropyl 16,17-dihydroapovincaminate, which melts at 69°–70° C, is thus collected.

$\alpha_D = +175°$ (chloroform).

This compound is soluble in ether, chloroform and methanol; its hemi-malate melts at 89°–90° C. It is readily soluble in water. Its purity was confirmed by thin layer chromatography on neutral silica gel (kieselgel H of thickness 0.25 mm) using, as eluants, methanol and chloroform (1 : 9); Rf = approximately 0.50.

Analysis of the hemi-malate $C_{27}H_{36}O_8N_2$: Calculated % C, 62.77; H, 7.02; N, 5.42; O, 24.77. Found % C, 62.69; H, 7.08; N, 5.50; O, 24.69.

U.V. spectrum

| $\lambda_{max}$ | 232 nm (log ε = 4.10) |
|---|---|
| | 282 nm (log ε = 3.60) |

I.R. spectrum Band at 1,740 cm$^{-1}$ (unconjugated ester) Wide band at 3,300 cm$^{-1}$ (combined alcohol group)

N.M.R. spectrum 0.83 ppm (signal from the ethyl side chain) 1.10 ppm (doublet (J = 6Hz) from the

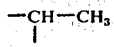

group), 4.55 ppm (approximately) (wide signal = axial hydrogen H in the 14-position).

EXAMPLE 2

Cis and trans isomers of ethyl 16,17-dihydroapovincaminate.

(The isomerism relates to the relative orientation of the ethyl chain in the eburnamenine skeleton and the ester group).

R = $C_2H_5$; code numbers: cis isomer SL B 827 trans isomer SL B 828

6.12 g of ethyl apovincaminate, 250 ml of pure acetic acid and 1 g of palladium chloride are introduced into a 500 ml round-bottomed wide-necked flask equipped with a three-way tap. This flask is connected to a hydrogenation apparatus and is purged several times. Hydrogenation is then effected, slowly, under atmospheric pressure and at ambient temperature, whilst stirring mechanically. When the theoretical amount of hydrogen has been absorbed, the catalyst is filtered off on Celite 545. The acetic acid solution is rendered alkaline by means of ammonia and is extracted with 250 ml of chloroform. The extract is dried over anhydrous sodium sulphate and the solvent is evaporated; the oil thus obtained in dried in vacuo over phosphorus pentoxide. The oil is purified on a column of alumina of activity II or III, eluting with benzene.

A 250 ml fraction is collected, and is evaporated to dryness. After drying, crystallisation is initiated by means of a drop of ether. Trans isomer (SL B 828 (16 α-H). The first crop of crystals, weighing 540 mg (yield ≃ 9%), comprises the trans isomer which melts at 146°–7° C. It forms colourless crystals which are insoluble in ether. Its purity is confirmed by thin layer chromatography on silica gel Merck G F 254, Rf = 0.62 (eluants: chloroform/methanol, 96:4).

Analysis: $C_{22}H_{28}N_2O_2$ Calculated %: C, 74.97; H, 8.01; N, 7.95; O, 9.08. Found: % C, 74.96; H, 7.96; N, 7.88; O, 9.14.

U.V. spectrum

| $\lambda_{max}$ | 277 nm (log ε = 3.89) |
|---|---|
| | 282 nm (log ε = 3.91) |
| | 291 nm (log ε = 3.83) |

I.R. spectrum Band at 1,750 cm$^{-1}$ (unconjugated ester), Band at 1,715 cm$^{-1}$.

N.M.R. spectrum No peak corresponding to ethylenic protons. Cis isomer (SL B 827) (16 β-H). Present in the second crop of crystals, weighing 2,391 g (yield ≃ 40%) and melting at 102°–103° C.

These crystals are yellowish and soluble in ether. Thin layer chromatography is effected under the same conditions as for the trans isomer. The Rf is also 0.62 and the compound is pure.

Analysis: $C_{21}H_{28}N_2O_2$ Calculated % : C, 74.97; H, 8.01; N, 7.95; O, 9.08. Found % : C, 75.01; H, 7.91; N, 7.90; O, 9.13.

U.V. spectrum

| $\lambda_{max}$ | 280 nm (log ε = 3.95) |
|---|---|
| | 285 nm (log ε = 3.98) |
| | 292 nm (log ε = 3.90) |

I.R. spectrum Band at 1,750 cm$^{-1}$ (unconjugated ester)

N.M.R. spectrum No peaks corresponding to ethylenic protons 4.80 ppm (quadruplet: axial hydrogen H in the 16-position).

The percentage analyses and most of the physical characteristics show that the two compounds are isomers which are very similar to one another; investigation of the N.M.R. spectrum shows that the isomerism depends on the configuration of the carbon atom in the 16-position. In the spectrum of SL B 828, the signal from the hydrogen atom carried by this carbon atom is masked by other absorptions and is revealed only by integration, whilst in the spectrum of SL B 827, this hydrogen atom appears at lower fields, in the form of a well resolved quadruplet at 480 ppm, the coupling constants of which, J = 8Hz and J' = 2Hz, indicate an axial conformation of the H in the 16-position, (corresponding to an α-orientation). From this information, it is deduced that SL B 827 possesses the equatorial ester group (the most stable conformation) whilst SL B 828 possesses the axial ester group; this is supported by the large difference in the yields (40% and 9% respectively).

The absolute configuration of these two esters can thus be written as:

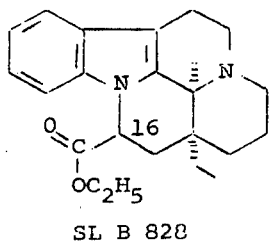

SL B 828 and

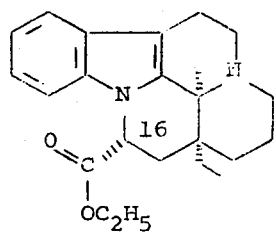

SL B 827

EXAMPLE 3

Prop-2'-ynyl 16,17-dihydroapovincaminate and its hydrochloride (R = —CH$_2$—C ≡ CH; code number of the hydrochloride: SL C 211)

4.3 g (0.036 mol) of thionyl chloride and 3 ml of pyridine are added, whilst stirring mechanically, to 10 g (0.0309 mol) of 16,17-dihydroapovincaminic acid suspended in 400 ml of anhydrous benzene. The mixture is stirred for 16 hours at ambient temperature. A further 6 ml of pyridine, followed by 1.75 g (0.0309 mol) of propargyl alcohol, are added to the solution of the acid chloride thus formed, and this mixture is heated for 1 hour at the reflux temperature. The mixture is evaporated to dryness, 500 ml of water are added to the oily residue, and the crystals formed are filtered off, washed with water, dried in vacuo and recrystallised from the minimum amount of isopropyl alcohol. 5.5 g (yield: 41%) of prop-2'-ynyl 16,17-dihydroapovincaminate hydrochloride are finally collected; melting point = 220° C.

Analysis: C$_{23}$H$_{27}$ClN$_2$O$_2$ (398.936) Calculated % : C, 69.25; H, 6.82; N, 7.02; Cl, 8.89; O, 8.02.

Calculated for 1.63% of H$_2$O (measured by the Karl Fischer method): C, 68.12; H, 6.89; N, 6.91; Cl, 8.71; O, 9.33. Found % : C, 68.09; H, 6.97; N, 6.78; Cl, 8.92; O, 9.22. C, 68.14; H, 6.97; N, 6.99; Cl, 8.88.

EXAMPLE 4

Propyl 16,17-dihydroapovincaminate and its oxalate (R = —CH$_2$—CH$_2$—CH$_3$; code number of the oxalate: SL C 250)

4 g (0.071 mol) of potassium hydroxide pellets are dissolved in a mixture of 100 ml of ethanol and 100 ml of hexamethylphosphorotriamide, and 20 g (0.0618 mol) of 16,17-dihydroapovincaminic acid are then added. The mixture is stirred until complete dissolution has taken place. 40 ml of 1-bromo-propane are added to the clear solution obtained, whilst continuing to stir, and the mixture is heated at 90° C for 2 hours. The mixture is cooled, the potassium chloride formed during the reaction is filtered off and the ethanol is evaporated under reduced pressure. The liquid residue is poured into 1,000 ml of water and extraction is effected 3 times in succession using 250 ml of ethyl acetate. The organic solutions are combined, washed with water and dried over sodium sulphate. They are then evaporated to dryness, the oily residue is dissolved in ethyl acetate and a solution of oxalic acid in the same solvent is added. The oxalate which has precipitated is filtered off and is crystallised from the minimum amount of 2-propanol. 21 g (yield: 75%) of propyl 16,17-dihydroapovincaminate oxalate are thus collected; melting point: 145° C.

Analysis: C$_{25}$H$_{32}$N$_2$O$_6$ (456.543) Calculated % : C, 65.77; H, 7.07; N, 6.14; O, 21.03. Found % : C, 65.56; H, 7.03; N, 6.44; O, 21.45. C, 65.68; H, 7.24; N, 6.23.

EXAMPLE 5

2'-Hydroxyethyl 16,17-dihydroapovincaminate and its oxalate (R = —CH$_2$CH$_2$OH; code number of the oxalate: SL C 290)

3.64 g (0.065 mol) of potassium hydroxide in 50 ml of methanol are added to a solution of 20 g (0.0593 mol) of 16,17-dihydroapovincamine in 200 ml of methanol, and this mixture is stirred for 16 hours at a temperature of 20° C. The mixture is evaporated to dryness and the residue is taken up several times in a small amount of benzene so as to obtain dry potassium 16,17-dihydroapovincaminate.

This salt is dissolved in 80 ml of anhydrous dimethylformamide and a solution of 4.774 g (0.0593 mol) of 2-chloro-ethanol in 20 ml of dimethylformamide is added gradually, with stirring. Whilst continuing to stir, the reaction mixture is heated at 100° C for 24 hours and is then cooled and poured into 1,000 ml of water. A precipitate is filtered off, dried and chromatographed on a column of silica gel H, eluting with a mixture of benzene and ethanol (8 – 2). The fractions containing unreacted 16,17-dihydroapovincamine, 10 g of which are recovered, are collected first, and then the fractions containing the ester are collected. The latter, which is in the form of a pale yellow resin, is dissolved in ethyl acetate and an excess of a solution of oxalic acid is added. The oxalate formed is filtered off and purified by dissolving it in boiling isopropyl alcohol; the hot solution is filtered, the filtrate is cooled and ether is added to it. 5.6 g (yield: 41%) of 2'-hydroxyethyl 16,17-dihydroapovincaminate oxalate are thus collected; the melting point of this product is not sharp, and it softens above 70° C.

Analysis: C$_{24}$H$_{30}$N$_2$O$_7$ (458.516) Calculated % : C, 62.87; H, 6.60; N, 6.11.

Calculated for 0.23% of H₂O (measured by the Karl Fischer method) % : C, 62.72; H, 6.61; N, 6.10. Found % : C, 62.40; 7.09; H, 5.90. C, 62.61; 6.65; H, 5.92.

EXAMPLE 6

2',3'-Dihydroxypropyl 16,17-dihydroapovincaminate

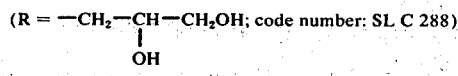

(R = —CH₂—CH—CH₂OH; code number: SL C 288)
         |
         OH 2.5 g (0.03 mol) of anhydrous pyridine, followed by 3.6 g (0.03 mol) of thionyl chloride, are added to a suspension of 9.7 g (0.03 mol) of 16,17-dihydroapovincaminic acid in 400 ml of anhydrous benzene. This mixture is stirred for 16 hours at ambient temperature, 4 g (0.03 mol) of 2,2-dimethyl-4-hydroxymethyl-1,3-dioxalane are then added, and the mixture is heated at the reflux temperature for 1 hour 30 minutes. The benzene is evaporated under reduced pressure and the residue is taken up twice in succession in a little toluene which is driven off under reduced pressure, thus entraining the pyridine. The resulting paste-like product is purified by passing it through a column of alumina, and eluting with dichloromethane. The fractions containing the ester are combined, the solvent is driven off and the residue is dissolved in 100 ml of water. Under a nitrogen atmosphere, 2 ml of a concentrated solution of hydrochloric acid are added, with stirring, and the mixture is heated at 90° C for 20 minutes. The solution is cooled and filtered, ethyl acetate is added and the aqueous layer is neutralised by adding a 10% solution of ammonia with stirring. The organic layer is isolated, the aqueous layer is extracted again with two 100 ml portions of ethyl acetate, the organic solutions are combined and dried over sodium sulphate, and the solvent is driven off under reduced pressure. A paste-like residue which solidifies in the desiccator is obtained. 6.6. g (yield: 56%) of 2',3'-dihydroxypropyl 16,17-dihydroapovincaminate are thus collected.

Analysis: $C_{23}H_{30}N_2O_4$ (398.506) Calculated % : C, 69.32; H, 7.59; N, 7.03.

Calculated for 1.75% of H₂O (measured by the Karl Fischer method) % : C, 68.12; H, 7.65; N, 6.91. Found % : C, 67.80; H, 7.60; N, 6.39. C, 68.01; H, 7.79; N, 6.48.

The compounds of the invention were subjected to a series of pharmacological experiments which demonstrated their valuable properties. The reference substance chosen was vincamine.

Acute toxicity

Swiss mice of the srain CDl were used and the 50% lethal doses of the compounds of the invention and of vincamine, administered by various methods (per os, intraperitoneally and intravenously), were determined graphically.

It was found that the compounds of the invention possessed toxicities of the same order of magnitude as that of vincamine.

Test involving anoxia, under sub-atmospheric pressure conditions, in mice

Mice (CDl strain) were kept in an atmosphere which was depleted of oxygen by creating a partial vacuum (190 mm of mercury, corresponding to 5.25% of oxygen).

The period of time for which the animals survived was noted; this period of time is increased by agents which can promote tissue oxygenation, and in particular cerebral oxygenation.

The compounds of the invention and vincamine were administered intraperitoneally, at several doses, ten minutes before the experiment. The percentage increases in the period of survival relative to the values obtained in the case of control animals were calculated, and the mean active dose (MAD), this being the dose which increases the period of survival by 100 percent, was determined graphically.

The results are given in Table I.

TABLE I

| Compounds (example) | Code number | MAD, intraperitoneal administration, mg/kg |
|---|---|---|
| 1 | SL B-826 | 4.3 |
| 2 (trans isomer) | SL B-828 | 3.5 |
| 3 | SL C 211 | 11 |
| 5 | SL C 290 | 7.7 |
| Vincamine | | 8 |

Test involving anoxia, under normal pressure conditions, in mice.

Mice (CDl strain) were kept individually in an atmosphere which was depleted of oxygen (oxygen content 4%) produced by mixing nitrogen and air, at atmospheric pressure, in a specially designed apparatus.

The period of time for which the animals survived was noted. This period of time is increased by agents which can promote tissue oxygenation, and in particular cerebral oxygenation. The compounds investigated were administered peritoneally, at several doses, ten minutes before the experiment. The percentage increases in the period of survival, relative to controls were calculated and the mean active dose (MAD), this being the dose which increases the period of survival by 100%, was determined graphically.

In this test, it was found that whilst the MAD of vincamine was 12 mg/kg, that of SL B-826 was 6 mg/kg.

In the particular experiments carried out, the compounds of the invention thus proved to be superior to vincamine. They are therefore of therapeutic value, especially in the cardiovascular and respiratory field.

The invention therefore also provides pharmaceutical compositions which contain the compounds (I) as active principles, in combination with any excipients suitable for administering them, particularly orally, parenterally or topically. These pharmaceutical compositions can also contain other medicinal substances with which the compounds (I) are pharmacologically and therapeutically compatible.

For oral administration, any of the usual forms suitable for this method of administration, such as tablets, dragees, gelatine-coated pills, capsules, cachets, and potable solutions or suspensions can be used. The unit dose of active principle is suitably 0.5 to 25 mg and the daily dose is suitably 0.5 to 200 mg.

An example of a composition which is particularly suitable for oral administration is one comprising a therapeutically effective amount of a compound of formula (I) and ascorbic acid and/or a salt thereof with a mineral or organic base and/or a complex thereof with an aromatic heterocyclic compound containing at least one ring nitrogen atom.

For parenteral administration, solutions prepared in advance or at the time of use, buffered to the physiological pH, can be used. These solutions suitably contain 0.5 to 20 mg of active principle in a volume of 1 to 5 ml. In practice, they can be dispensed into ampoules of capacity 1 to 5 ml, for administration by intramuscular or intravenous injection, or for administration by slow intravenous infusion.

The daily dose administered parenterally is suitably 0.5 to 100 mg.

For topical administration, lotions, emulsions, ointments or creams, the nature of which promotes cutaneous penetration, can be used.

We claim:
1. 2'-Hydroxypropyl-16,17-dihydroapovincaminate or its hemi-malate.
2. Propyl-16,17-dihydroapovincaminate or its oxalate.
3. 2'-Hydroxyethyl-16,17-dihydroapovincaminate or its oxalate.

* * * * *